United States Patent [19]

Garst et al.

[11] Patent Number: 5,476,872
[45] Date of Patent: Dec. 19, 1995

[54] 1,11-DIESTERS OF PROSTAGLANDIN-$F_{2\alpha}$ HAVING A POLAR ESTER GROUP AT C-1

[75] Inventors: Michael E. Garst, Newport Beach; Elizabeth T. Syage, Cypress; Michael B. Roof, Los Angeles; David F. Woodward, El Toro; Ming Fai Chan, San Diego, all of Calif.

[73] Assignee: Allergan, Inc., Irvine, Calif.

[21] Appl. No.: 138,274

[22] Filed: Oct. 18, 1993

[51] Int. Cl.[6] ........................ A61K 31/557; C07C 405/00
[52] U.S. Cl. .............................. 514/530; 560/121
[58] Field of Search ............................. 514/530; 560/121

[56] References Cited

U.S. PATENT DOCUMENTS

| | | | |
|---|---|---|---|
| 4,599,353 | 7/1986 | Bito | 514/530 |
| 4,994,274 | 2/1991 | Chan et al. | 424/427 |
| 5,034,413 | 7/1991 | Chan et al. | 514/530 |
| 5,139,491 | 8/1992 | Chan et al. | 604/294 |
| 5,238,961 | 8/1993 | Woodward et al. | 514/573 |
| 5,288,754 | 2/1994 | Woodward | 514/530 |

FOREIGN PATENT DOCUMENTS

| | | | |
|---|---|---|---|
| 0364417 | 4/1990 | European Pat. Off. | A61K 31/557 |
| 0410785 | 1/1991 | European Pat. Off. | A61K 31/557 |

OTHER PUBLICATIONS

Bito, L. Z., *Arch. Ophthalmol*, 105, 1036 (1987).
Bito, L. Z. *Applied Pharmacology in the Medical Treatment of Glaucomas*, Drance, S. M. and Neufeld, A. H. eds., New York, Grune & Stratton, 1984 pp. 477–505).
Bito, L. Z., *Biological Protection with Prostaglandins*, Cohen, M. M., ed., Boca Raton Fla. CRC Press Inc., 1985, pp. 231–252.
M. S. Starr, *Exp. Eye Res.* 11, 170–177 (1971).
Nilsson et al., *Invest, Ophthalmol. Vis. Sci.* 28 (suppl), 284 (1987).
Siebold et al., *Prodrug* 5, 3 (1989).
Woodward, et al., Prostaglandin $F_{2a}$ Effects on Intraocular Pressure Negatively Correlate with FP–Receptor Stimulation, *Investigative Ophthalmology & Visual Science*, vol. 30, No. 8, Aug. 1989.
Zajacz, et al., Effect on Human Eye of Prostaglandin and a Prostaglandin Analogue Used to Induce Abortion, The Eye: Reproduction, *Obstetrics and Gynecology*, 4, 316 (1976).

*Primary Examiner*—Robert Gerstl
*Attorney, Agent, or Firm*—Gabor L. Szekeres; Robert J. Baran; Martin A. Voet

[57] ABSTRACT

Compounds of the formula

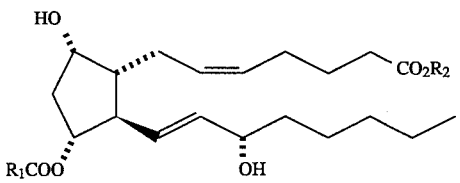

where the hatched lines indicate alpha ($\alpha$) configuration, a solid triangle is used to indicate beta ($\beta$) configuration, lines on both sides of a double bond indicate cis (Z) configuration, and lines on opposite sides of the double bond indicate trans (E) configuration; $R_1$ is alkyl of 1–10 carbons, $C_1$–$C_{10}$alkylphenyl, phenyl-$C_1$–$C_{10}$alkyl, or alkenyl of 2 to 10 carbons and having 1 to 3 double bonds; $R_2$ is Z—$OR_3$, Z—$OCOR_3$, Z—$OCONHR_3$, Z—$OCOOR_3$, Z—$NR_4R_5$, Z—$NR_4COR_3$, Z—$NR_4SO_2R_3$, Z—$COOR_3$, Z—$CONR_4R_5$, Z—CHO; Z is $(CH_2)_n$ where n is 1–6, or Z is an alkenyl group having 2 to 6 carbons and 1 or 2 double bonds, $R_3$ is H, alkyl of 1–6 carbons, alkenyl of 2 to 6 carbons or phenyl, $R_4$ and $R_5$ independently are H or alkyl of 1 to 6 carbons, have ocular hypotensive activity.

3 Claims, No Drawings

1,11-DIESTERS OF PROSTAGLANDIN-$F_{2\alpha}$ HAVING A POLAR ESTER GROUP AT C-1

BACKGROUND OF THE INVENTION

1. Field of the Invention

The present invention is directed to 1,11-diesters of prostaglandin $F2\alpha$ which have a polar ester group at the C-1 position. The compounds are active as agents for decreasing intraocular pressure in the mammalian eye.

2. Background Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical B-adrenoreceptor antagonists have traditionally been the drugs of choice for treating glaucoma.

Prostaglandins can be described as derivatives of prostanoic acid, the structure and numbering of which is shown in Formula 1. The term prostaglandin $F2\alpha$ describes a prostaglandin compound which has the structure shown in Formula 2.

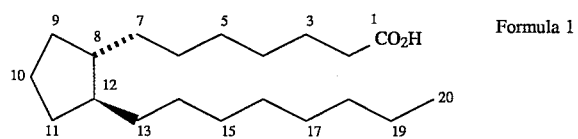

Formula 1

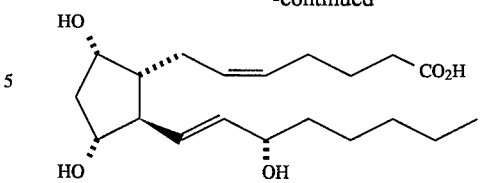

Formula 2

Prostagladins were earlier regarded as potent ocular hypertensives; however, evidence accumulated in the last two decades shows that some prostaglandins are highly effective ocular hypotensive agents and are ideally suited for the long-term medical management of glaucoma. (See, for example, M. S. Starr, *Exp. Eye Res.* 11, 170–177, (1971); Bito, L. Z. *Biological Protection with Prostaglandisn* Cohen, M. M., ed., Boca Raton, Fla. CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostagladins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest, Ophthalmol. Vis. Sci.* 28 (suppl), 284 (1987)].

The isopropyl ester of $PGF_{2\alpha}$ has been shown to have significantly greater hypotensive potency than the parent compounds, which was attributed to its more effective penetration through the cornea. In 1987 this compound was described as "the most potent ocular hyptensive agent ever reported." [See, for example, Bito, L. Z., *Arch. Ophthalmol,* 105, 1036 (1987), and Siebold et al., *Prodrug* 5, 3 (1989)].

Whereas prostagladins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of postaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 596,430 relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 967,586. Similarly, 11,15- 9,15 - and 9,11-diesters of prostaglandins, for example 11,15-dipivaloyl $PGF_{2\alpha}$ are known to have ocular hypotensive activity. See U.S. Pat. No. 4,494,274; co-pending application 584,370, and U.S. Pat. No. 5,034,413.

U.S. Pat. No. 5,139,491 assigned to Allergan Inc. discloses 2-decarboxyl-2-alkoxyalkyl prostaglandins, including for example 2-decarboxyl-2-methoxymethyl prostaglandin $F_{2\alpha}$ as ocular hypotensive agents. Co-pending application Ser. No. 07/538,204 filed on Jun. 14, 1990 (now allowed) discloses PGF 1-alcohols.

Generally speaking, whereas derivatives of prostaglandin $F_{2\alpha}$ where the 11-OH group is acylated and the 1-COOH group is alkylated have intraocular hypotensive activity, these compounds have low solubility in water. It is therefore desirable to provide such further prostaglandin $F_{2\alpha}$ derivatives which have reasonable aqueous solubility coupled with intraocular hypotensive activity.

SUMMARY OF THE INVENTION

Novel compounds of the present invention are shown in Formula 3

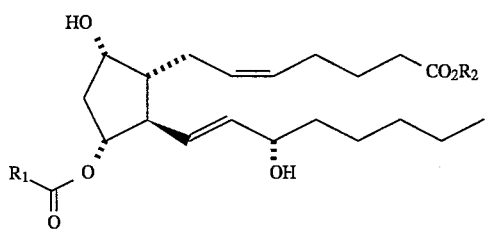

Formula 3 where the hatched lines indicate alpha ($\alpha$) configuration, a solid triangle is used to indicate beta ($\beta$) configuration, lines on both sides of a double bond indicate cis (Z) configuration, and lines on opposite sides of the double bond indicate trans (E) configuration;

$R_1$ is alkyl of 1–10 carbons, $C_1$–$C_{10}$alkylphenyl, phenyl-$C_1$–$C_{10}$alkyl, or alkenyl of 2 to 10 carbons and having 1 to 3 double bonds;

| $R_2$ is | Z—$OR_3$, |
| --- | --- |
| | Z—$OCOR_3$, |
| Z—$OCONHR_3$, | |
| Z—$OCOOR_3$, | |
| Z—$NR_4R_5$, | |
| Z—$NR_4COR_3$, | |
| Z—$NR_4SO_2R_3$, | |
| Z—$COOR_3$, | |
| Z—$CONR_4R_5$, | |
| Z—CHO; | |

Z is $(CH_2)_n$ where n is 1–6, or Z is an alkenyl group having 1 to 6 carbons and 1 or 2 double bonds, $R_3$ is H, alkyl of 1–6 carbons, alkenyl of 2 to 6 carbons or phenyl, $R_4$ and $R_5$ independently are H or alkyl of 1 to 6 carbons.

In another aspect the present invention relates to pharmaceutical compositions containing as active ingredient one or more compounds of the present invention (or their pharmaceutically acceptable salts).

In still another aspect the present invention relates to methods of administering to a mammal a pharmaceutical composition having as its active ingredient one or more compounds of Formula 3 (or their pharmaceutically acceptable salts) for the purpose of lowering intraocular pressure in the eye of the mammal.

DETAILED DESCRIPTION OF THE INVENTION

General Embodiments

The present invention relates to novel compounds of Formula 3, and to their use in pharmaceutical compositions and methods for the purpose of lowering intraocular pressure in the eye of a mammal.

Definitions

In Formula 3 as well as in all other chemical formulas in the present application for United States letters patent, bonds shown with hatched lines indicate a bond below the plane of the paper, thus signifying alpha ($\alpha$) configuration; bonds shown as a solid triangle indicate a bond above the plane of the paper, thus signifying beta ($\beta$) configuration; Trans (E) configuration of substituents about a double bond is indicated by bonds pointing in opposite directions about a double bond, whereas cis (Z) configuration of substituents about a double bond is indicated by bonds pointing in the same direction about a double bond.

The term alkyl refers to and covers any and all groups which are known as normal alkyl, branch-chain alkyl and cycloalkyl. Lower alkyl means the above-defined broad definition of alkyl groups having 1 to 6 carbons, and as applicable, 3 to 6 carbons for branch chained and cyclo-alkyl groups.

The term "ester" as used here refers to and covers any compound falling within the definition of that term classically used in organic chemistry. Amide has the meaning classically accorded that term in organic chemistry. In this instance it includes but is not limited to unsubstituted amides and aliphatic mono- and di-substituted amides.

A pharmaceutically acceptable salt may be prepared for any compound used in the method of treatment of this invention, if the compound has a functionality capable of forming such salt, for example an acid functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethanine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

In addition to the double bonds which are specifically shown in Formula 3 and the configuration of which is indicated in the formula, the compounds of the present invention may contain additional double bonds in the $R_1$ and $R_2$ substituents and therefore can have trans and cis (E and Z) isomers. In addition, the compounds of the present invention contain one or more chiral centers and therefore exist in enantiomeric and diastereomeric forms. Unless the structural formula or the language of this application specifically designate a particular cis or trans isomer or a particular configuration of a chiral center, the scope of the present invention is intended to cover all such isomers per se, as well as mixtures of cis and trans isomers, mixtures of diastereomers and racemic mixtures of enantiomers (optical isomers) as well.

For the sake of ease of description, that side chain in the formulas of the prostagladin derivatives described here which contains 7-carbons is sometimes referred to in this application as the "α side chain", and the other side chain attached to the cyclopentane or cyclopentene ring is sometimes called as the "Ω side chain". This nomenclature is in accord with standard usage in prostaglandin chemistry.

General Description of the Compounds of the Invention

Referring now to the structure shown in Formula 3, the 5,6 double bond in the α side chain is in cis (Z) and the 13,14 double bond in the Ω side chain is in trans (E) configuration. The 9 and 15 hydroxyl groups are in α positions, and the 11-substituent group is also in the α position. Those skilled in the art will recognize that the foregoing configurations are those of prostaglandin $F_{2\alpha}$. In accordance with the present invention the C-11 hydroxyl group is esterified with an $R_1CO-$ function as defined in connection with Formula 3. Preferably the $R_1$ group is lower alkyl, and more preferably branched chain alkyl.

The C-1 carboxyl group of the compounds of the present invention is also esterified with an $R_2$ group which has a polar function or region. Surprisingly, these compounds retain the ocular hypotensive properties of related prostglandin $F_{2\alpha}$ derivatives, but also have increased aqueous solubility, which renders them particularly suitable for use as topical ocular hypotensive agents. The polar groups or regions in the $R_2$ group of the compounds of the present invention are defined in connection with Formula 3. Generally speaking, the alkyl or alkenyl group which alkylates the 1-carboxyl function in the compounds of the invention has a hydroxyl, ester, carbamate, carbonate, amine, amide, sulfonamide, carboxylic acid, or aldehyde functionality. Preferably the $R_2$ group includes a hydroxy alkyl (($CH_2)_n-$OH) or an alkanoic acid amide (($CH_2)_n-CONH_2$) functionality where n is 1 to 4.

The most preferred compounds of the invention are shown in Table 1 with reference to Formula 3.

TABLE 1

| Compound # | $R_1$ | $R_2$ |
|---|---|---|
| 1 | $(CH_3)_3C$ | $(CH_2)_2OH$ |
| 2 | $(CH_3)_3C$ | $(CH_2)CONH_2$ |

Methods of Administration, Formulations

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisol and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop is about 20-35 μl.

Biological Activity

The ability of a pharmaceutical composition which contains a compound of Formula 3 to lower intraocular pressure in the eye of a mammal, can be demonstrated by an assay performed on the eyes of dogs. The assay is descibed as follows: male and female beagle dogs weighing 10-15 kg had been trained for a minimum of 2 months so that intraocular pressure could be measured without the use of restraining devices. Intraocular pressure was measured by pneumatonometry using applanation tonometers (Alcon). One minute prior to tonometry, 25 μl of proparacaine (Allergan, Irvine Calif.) was applied to minimize ocular discomfort during the procedure. Determination of the effects of the compounds of the invention on intraocular pressure involved administration of 1 to 25 μl of solution of the compound to one eye and an equal volume of vehicle to the contralateral eye as a control.

The effect of the compounds of the invention to lower intraocular pressure in dog eyes at 2, 3, 4, and 6 hours after administration of the test compound, in accordance with the above-described assay is shown in Table 2 with respect to compounds 1 and 2 of the present invention, and for reference compound prostaglandin $2F_{2\alpha}$-1-isopropyl, 11 pivaloyl diester which is a known potent ocular hypotensive agent. This reference compound (abbreviated refer. cmp. in Table 1) differs from the compounds of the present invention in the nature of the moiety which forms an ester with the 1-carboxylic acid function.

TABLE 2

| Compound # | Weight/by Volume Concentration | Change in IOP (mm of Hg) | | | |
|---|---|---|---|---|---|
| | | 2 hr | 3 hr | 4 hr | 6 hr |
| 1 | 0.001 | −4.0 | −4.7 | −3.5 | −2.6 |
| 1 | 0.01 | +0.7 | −3.0 | −5.7 | −7.7 |
| 1 | 0.1 | — | +1.9 | −2.4 | −7.8 |
| 2 | 0.01 | −3.0 | −2.4 | −2.8 | −1.8 |
| 2 | 0.1 | −2.1 | −2.4 | −4.2 | −1.9 |
| refer. cmp. | 0.001 | −5.3 | — | 0 | −0.2 |
| refer. cmp. | 0.01 | −6.9 | −5.4 | −3.7 | −2.7 |
| refer. cmp. | 0.1 | — | — | −1.7 | −5.0 |

General Description of Synthetic Procedures

The compounds of the invention can be made by a number of different synthetic chemical pathways. To illustrate the invention, the following detailed description is provided. The synthetic chemist will readily appreciate that the conditions set out here are specific embodiments which can be generalized to obtain any and all compounds described in the present specification.

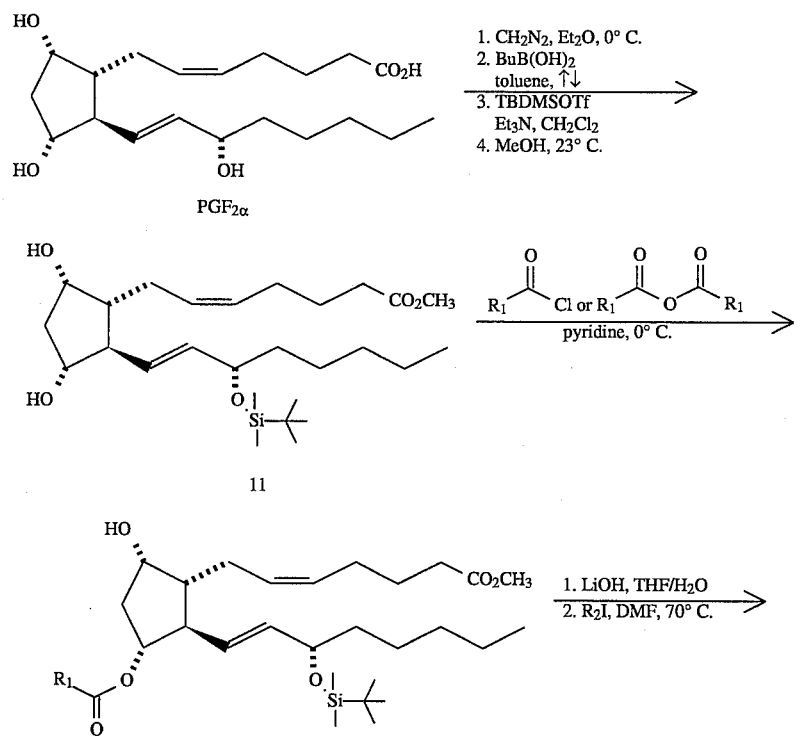

Scheme I

-continued
Scheme I

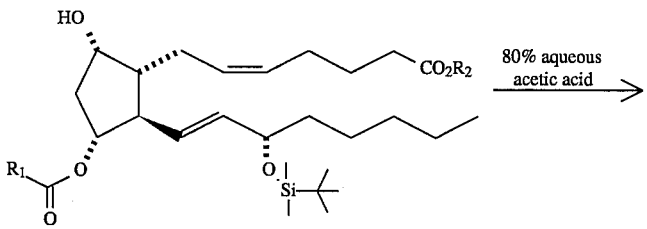

Formula 5

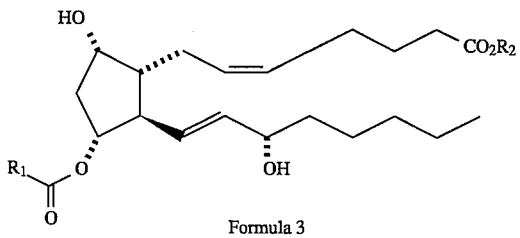

Formula 3

Referring now to Reaction Scheme 1 the starting material is prostaglandin $F_{2\alpha}$ ($PGF_{2\alpha}$) which is readily available commercially or can be obtained by known literature procedures. As it should already be apparent to those skilled in the art based on the preceding description of the compounds of the invention, the purpose of the reactions shown in Reaction Scheme 1 is to selectively esterify the 11-hydroxyl group of $PGF_{2\alpha}$ with an $R_1$—CO group ($R_1$ is defined as above) and to form a 1-carboxylate ester with the $R_2$ group ($R_2$ is defined as above). To this end in the preferred process of synthesis depicted in Reaction Scheme 1, $PGF_{2\alpha}$ is first methylated in the C-1 carboxylate function with diazomethane, and thereafter the 9 and 11 hydroxyl groups are protected by treatment with n-butyl boronic acid. Reaction with t-butyldimethylsilyl trifluoromethylsulfonate results in protection of the 15 hydroxyl group, and thereafter reaction with methyl alcohol removes the n-butyl boronate protective group from the 9, and 11 hydroxyl funtions. The resulting 15-t-butyldimethylsilyloxy-$PGF_{2\alpha}$ methyl ester (Compound 11) is reacted with an acyl chloride of the formula $R_1COCl$, or with an acid anhydride of the formula $(R_1CO)_2O$ in a suitable solvent, such as pyridine, to provide a compound of Formula 4, namely the 11-ester of 15-t-butyldimethylsilyloxy-$PGF_{2\alpha}$ methyl ester. The carboxylate ester function in the C-1 position is thereafter selectively saponified, for example by treatment with lithium hydroxyde to provide a free carboxylic acid in the C-1 position. The $R_2$ group (as defined in connection with Formula 3) is thereafter introduced by an alkylating agent which is characterized by the formula $R_2$—X wherein X is halogen, preferably iodine, or other suitable "leaving group". In the synthetic process leading to the preparation of preferred compound 1 of this invention the reagent $R_2$—X is 2-hydroxy-iodoethane, whereas for the preparation of Compound 2 the reagent is 2-iodoacetamide. The 15-t-butyldimethylsilyloxy-$PGF_{2\alpha}$-1, 11-diester of Formula 5 is thereafter subjected to mild acidic conditions to remove the t-butyldimethylsilyl protective group and to yield the compounds of the invention (Formula 3).

Specific Examples

Prostaglandin $F_2$ C-1 Methyl Ester

Prostaglandin $F_2$ (1.00 g, 2.83 mmol) was dissolved in a 1:1 mixture of methanol and ethyl acetate (2 ml of each) and stirred at 0° C. for several minutes. Diazomethane was then added dropwise until a yellow color persisted. The reaction was allowed to warm-up to room temperature and stir for an additional 30 minutes. The solvents were evaporated to dryness to yield 1.078 gm of the title compound.

Prostaglandin $F_2$, 9,11-n-butylboranoate, C-1-methyl Ester

Prostaglandin $F_2$ methyl ester (1.078g, 29 mmoles) was dissolved in methylene chloride (2.9 ml) and then n-butyl-boronic acid (0.359 g, 3.55 mmoles) was added. The reaction mixture was refluxed for 1 hour 15 minutes. The solvents were then evaporated to dryness to yield the title compound (1.27 gm).

Prostaglandin $F_2$ 9,11-n-butylboronate, 15-t-butyldimethylsilyl, C-1 Methyl Ester Prostaglandin $F_2$ 9,11-n-butyl boronate C-1 methyl ester (1.27 gm, 2.9 mmoles) was dissolved in methylene chloride (2.9 ml) and pyridine (0.80 ml) and stirred at 0° C. for several minutes. T-butyldimethylsilyl trifluoromethylsulfonate (1.33 ml 2.9 mmol) was then added dropwise for minutes and the entire reaction stirred overnight at room temperature. After about 15 hours the reaction was worked up using 10% citric acid, $NaHCO_3$, brine and ethyl acetate. The aqueous layer was extracted 3 times using EtoAc, and the combined organic phases were dried ($MgSO_4$) and evaporated to dryness to yield the title compound (1.712 gm).

15-t-Butyldimethylsilyloxy-$PGF_2$ Methyl Ester (Compound 11)

$PGF_2$ 9,11-n-butylboronate, 15-t-butyldimethylsilyl, C-1-methyl ester (1.7 g, 3.3 mmols) was dissolved in $CH_3OH$ (6 ml) and stirred at room temperature. Samples taken for $^1H$ NMR indicated the boronate for up to 24 hours. After 28 hours $^1H$ NMR showed complete loss of the boronate. Then the solvent methanol was evaporated to dryness, and the residue was purified on a silica gel column using 40% EtOAc/$CHCl_3$, to yield the title compound (0.876 g).

$^1H$ NMR ($CDCl_3$, 300 MHz) δ 5.3–5.55 (m, 4H), 4.18 (brs, 1H), 4.04 (q, J=6.1 Hz, 1H), 3.95 (brs, 1H), 3.66 (5, 3H), 2.31 (t, J=7.5 Hz, 2H), 2.03–2.35 (m, 8H), 1.20–1.83 (m, 12H), 0.88 (s with hidden mult., 12H), 0.03 (s, 3H), 0.01 (s, 3H).

15-t-Butyldimethylsilyloxy-11-pivaloyl PGF₂ Methyl Ester 15-t-Butyldimethylsilyloxy-PGF₂ methyl ester (Compound 11), 0.876 g, 1.87 mmoles) was dissolved in pyridine (3.7 ml) and stirred at 0° C. for several minutes. Pivaloyl chloride (0.28 ml 2.25 mmol) was then added slowly and the reaction mixture was stirred at 0° C. for 1 hour. The reaction mixture was then placed in the refrigerator for overnight. Thereafter the reaction mixture was worked up by evaporating the pyridine in vacuo, and by adding to the residue 10% citric acid, solution, brine and EtOAc. The aqueous layer was further extracted (three times 10 mls) with EtOAc and the combined organic layers were dried (MgSO₄) and evaporated to dryness to yield the title compound (1.05 gm, crude). A pure sample was obtained by silica column chromatography, using 20% to 40% EtOAc/hexanes as elvent.

$^1$H NMR (CDCl₃, 300 MHz) δ 5.3–5.5 (m, 4H), 4.77 (m, 1H), 4.12 (t, J=4.5 Hz, 1H), 4.01 (q, J=6.2 Hz, 1H), 3.63 (s, 3H), 2.0–2.56 (m, 7H), 2.28 (t, J=7.3 Hz, 2H), 1.1–1.7 (m, 12H), 1.14 (s, 9H), 0.84 (s, and hidden t, 12H), 0.0 (s, 6H).

15-t-Butyldimethylsilyloxy-11-pivaloyl PGF₂

15-t-Butyldimethylsilyloxy-11-pivaloyl-PGF₂ methyl ester (0.695 g, 1.30 mmols) was dissolved in tetrahydrofuran (7.8 ml) and then lithium hydroxide (0.5M sol. 3.9 ml, 1.95 mmol) was added. The reaction mixture was stirred at room temperature for 8 hours. The reaction was then worked up by adding 10% citric acid, solution, brine and EtOAc. The organic layer was dried (MgSO₄) and evaporated to dryness to yield crude title compound (949 mg). The crude product was purified on silica gel column using 40% EtOAc/hexanes as element.

15-t-Butyldimethylsilyloxy-11-pivaloyl PGF2 Glycolamide 15-t-Butyldimethylsilyloxy-11-pivaloyl PGF₂d (72 mg, 0.139 mmol) was dissolved in dimethylformamide (0.3 ml) and ethyldiisorpropylamine (0.030 ml) was added, followed several minutes later by iodoacetamide (39 mg, 0.209 mmol). The reaction mixture was stirred at room temperature for 19 hours. The reaction was then worked up by evaporating off the solvents in vacuo. To the remaining residue was added 10% aqueous citric acid solution and EtOAc. The aqueous layer was extracted with EtOAc (3×~10 mls) and the combined organic layers were dried (MgSO₄) and evaporated to dryness to yield the crude title compound (523 mg). The crude product was purified by chromatography on silica gel, using 60% EtOAc/hexanes as the eluent.

15t-Butyldimethylsilyloxy-11-pivaloyl PGF₂ 2-hydroxyethyl Ester 15-t-Butyldimethylsilyloxy-11-pivaloyl PGF₂ (82 mg, 0.158 mmol) was dissolved in dimethylforamide (0.3 ml) followed by ethyldiisopropylamine (0,055 ml, 2 mmol). The reaction mixture was stirred at 70° C. for several minutes at which time 2-iodoethylalcohol (0.025 ml, 54 mg, 2.0 mmol) was added. The reaction mixture was stirred for 6 hours at 70° C. and then overnight at room temperature (total 24 hours). The solvent and volatile components were evaporated in vacuo. To the residue was added 10% aqueous citric acid solution, brine and EtOAc. The aqueous layer was extracted (3×~10 ml). The combined organic layers were dried (MgSO₄) and evaporated to dryness to yield the title compound (36 mgs) is 98% yield.

11-Pivaloyl-PGF₂ Glycolamide 15-t-Butyldimethylsilyloxy-11-pivaloyl PGF₂ glycolamide (25.2 mg, 0.044 mmoles) was dissolved in tetrahydrofuran (0.29 ml) and then acetic acid (0.85 ml) and water (0.24 ml) were added. After 6 hours at room temperature a significant amount of starting material was still present, so 0.20 ml of additional acetic acid was added. The reaction mixture was stirred overnight and was worked up the next morning by addition of 10% aqueous citric acid solution, brine and EtoAc. The aqueous layer was extracted three times with EtOAc. The combined organic layers were dried (MgSO₄) and evaporated to dryness to yield the title compound as a clear oil. The title compound was further purified by chromatography on silica gel using 6% CH₃OH/CH₂Cl₂ as the eluent.

$^1$H NMR (300 MHz, CDCl₃) δ 5.85–6.25 (m, 2H), 5.37–5.52 (m, 4H), 4.81–4.83 (m, 1H), 4.54 (s, 2H), 4.13– 4.15 (m, 1H), 3.91–4.10 (m, 1H), 1.19–2.53 (m, 22H), 1.14 (s, 9H), 0.85 (t, J=6.8 Hz, 3H).

11-Pivaloyl-PGF₂-2-hydroxyethyl Ester 15-t-Butyldimethylsilyloxy-11-pivaloyl-PGF₂- 2-hydroxyethyl ester (27 mg, 0.048 mmol) was dissolved in tetrahydrofuran (0.20 ml) and then acetic acid (0.78 ml) and water (0.20 ml) were added. After 6 hours at room temperature a significant amount of starting material was still present, so 0.20 mls of additional AcOH was added. The reaction mixture was stirred overnight and was worked up the next morning by addition of 10% aqueous citric acid solution, EtoAc and brine. The aqueous layer was extracted three times with EtoAc. The combined organic layers were dried (MgSO₄) and evaporated to dryness to yield the crude title product as a clear oil. The title compound was further purified by chromatography on silica gel using 5% CH₃OH/CH₂Cl₂ as the elvent.

$^1$H NMR (300 MHz, CDCl₃) δ 5.38 –5.52 (m, 4H), 4.72–4.93 (m, 1H), 4.16–4.20 (m, 2H), 4.16–4.19 (m, 1H), 1.26–2.49 (m, 26H), 1.15 (s, 9H), 0.85 (t, J= 6.7 Hz, 3H).

What is claimed is:

1. A compound which is selected from a group consisting of 11-pivaloyl prostaglandin F₂α glycolamide and 11-pivaloyl prostaglandin F₂α hydroxyethyl ester.

2. A method of treating ocular hypertension which comprises applying to the eye a pharmaceutical composition, said composition comprising an amount sufficient to treat ocular hypertension of a compound which is selected from a group consisting of 11-pivaloyl prostaglandin F2α glycolamide and 11-pivaloyl prostaglandin F₂α hydroxyethyl ester.

3. A pharmaceutical product comprising an ophthalmic solution for the treatment of ocular hypertension, said solution comprising an amount sufficient to treat ocular hypertension of a compound which is selected from a group consisting of 11-pivaloyl prostaglandin F₂α glycolamide and 11-pivaloyl prostaglandin F₂α hydroxyethyl ester.

* * * * *

UNITED STATES PATENT AND TRADEMARK OFFICE
CERTIFICATE OF CORRECTION

PATENT NO. : 5,476,872
DATED : December 19, 1995
INVENTOR(S) : Garst et al.

It is certified that error appears in the above-indentified patent and that said Letters Patent is hereby corrected as shown below:

Column 1, line 9, "F2α" should be --$F_{2\alpha}$--;

Column 1, line 57, "F2α" should be --$F_{2\alpha}$--;

Column 9, line 45, "(R1CO)$_2$O" should be --$(R_1CO)_2O$--;

Column 11, line 50, "0,055" should be --0.055--;

Column 12, line 48, "F2α" should be --$F_{2\alpha}$--.

UNITED STATES PATENT AND TRADEMARK OFFICE
CERTIFICATE OF CORRECTION

PATENT NO. : 5,476,872
DATED : December 19, 1995
INVENTOR(S) : Garst et al.

It is certified that error appears in the above-indentified patent and that said Letters Patent is hereby corrected as shown below:

Column 10, line 49, "EtoAc" should be --EtOAc--;

Column 11, line 3, before "0.876)" please add --(--;

Column 11, line 26, "EtoAc" should be --EtOAc--;

Column 12, line 12, "EtoAc" should be --EtOAc--;

Column 12, line 31, "EtoAc" should be --EtOAc--;

Column 12, line 32, "EtoAc" should be --EtOAc--.

Signed and Sealed this

Twenty-fifth Day of February, 1997

Attest:

BRUCE LEHMAN

*Attesting Officer*    *Commissioner of Patents and Trademarks*